United States Patent [19]
Honigs et al.

[11] Patent Number: 6,151,517
[45] Date of Patent: Nov. 21, 2000

[54] METHOD AND APPARATUS FOR NONINVASIVE QUANTITATIVE MEASUREMENT OF BLOOD ANALYTES

[75] Inventors: David E. Honigs, Hagerstown; Robert D. Rosenthal, Montgomery Village, both of Md.

[73] Assignee: Futrex Inc., Gaithersburg, Md.

[21] Appl. No.: 09/235,286

[22] Filed: Jan. 22, 1999

[51] Int. Cl.⁷ ........................................................ A61B 5/00
[52] U.S. Cl. .......................... 600/322; 600/316; 600/336
[58] Field of Search ..................................... 600/310, 316, 600/322, 323, 330, 331, 336, 473, 476

[56] References Cited

U.S. PATENT DOCUMENTS 5,028,787   7/1991  Rosenthal et al. .
5,077,476  12/1991  Rosenthal .
5,216,598   6/1993  Branstetter et al. .................... 600/330
5,582,169  12/1996  Oda et al. .............................. 600/310
5,706,821   1/1998  Matcher et al. ........................ 600/310

*Primary Examiner*—Eric F. Winakur
*Attorney, Agent, or Firm*—Rothwell, Figg, Ernst & Manbeck

[57] ABSTRACT

A method and apparatus for performing quantitative noninvasive measurement of blood analytes, includes correction for measurement interference caused by pulse beat and changing body chemistry associated with blood circulation through the part of the body being measured as a function of time. A hypoglycemia monitor and alarm is provided which takes advantage of the methods described for separating pulse beat information from the measurement signals.

14 Claims, 14 Drawing Sheets

METHOD AND APPARATUS FOR NONINVASIVE QUANTITATIVE MEASUREMENT OF BLOOD ANALYTES

BACKGROUND OF THE INVENTION

FIELD OF THE INVENTION AND BACKGROUND

This invention relates to instruments for the non-invasive quantitative and semi-quantitative measurement of constituents in blood, such as blood glucose levels. Specifically, this invention relates to an improved analysis instrument for measurement of the near-infrared energy absorption of a body part, typically a finger, which is being irradiated with near-infrared energy for measurement of the blood analyte levels.

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions. In particular, the non-invasive near-infrared quantitative measurement apparatus has particular application for use by diabetics in monitoring the level of glucose in the blood.

U.S. Pat. No. 5,028,787, incorporated by reference herein, teaches the use of near-infrared (NIR) analysis techniques in which NIR radiant energy at bandwidths centering on one or more wavelengths of interest is passed through the skin of a subject. A portion of the energy re-emerges from the subject and is detected by a detector. The detector generates an output signal which is processed in accordance with NIR quantitative analysis algorithms to determine the concentration of selected blood analytes in the subject. The calculated concentration is then displayed on a display device provided on the instrument.

In U.S. Pat. No. 5,077,476, also incorporated by reference herein, it is taught that noninvasive blood glucose measurement can be made by transmitting near-infrared light through an extremity of the body, e.g., the most distal portion of the index finger.

One important aspect of the noninvasive blood analyte measurement technology disclosed in the referenced patents is the ability to calibrate the instruments so that quantitative measurements within acceptable accuracy and precision tolerances may be made over an extended period of time.

Figure 1A:
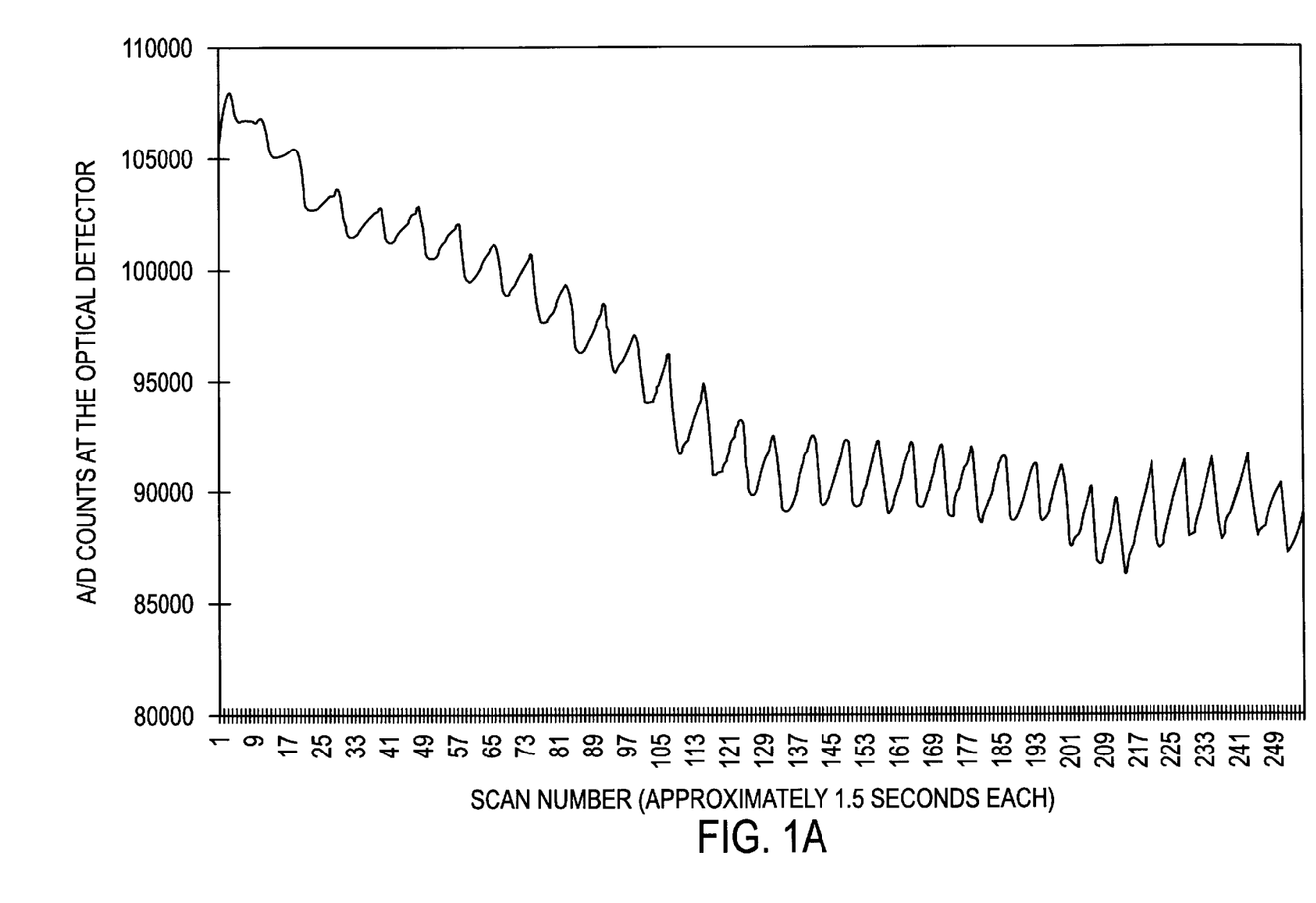
FIGS. 1A and 1B are graphs illustrating the effect of pulse beat on received optical measurement data in a noninvasive quantitative blood analyte measurement instrument during multiple scans.
Figure 1B:
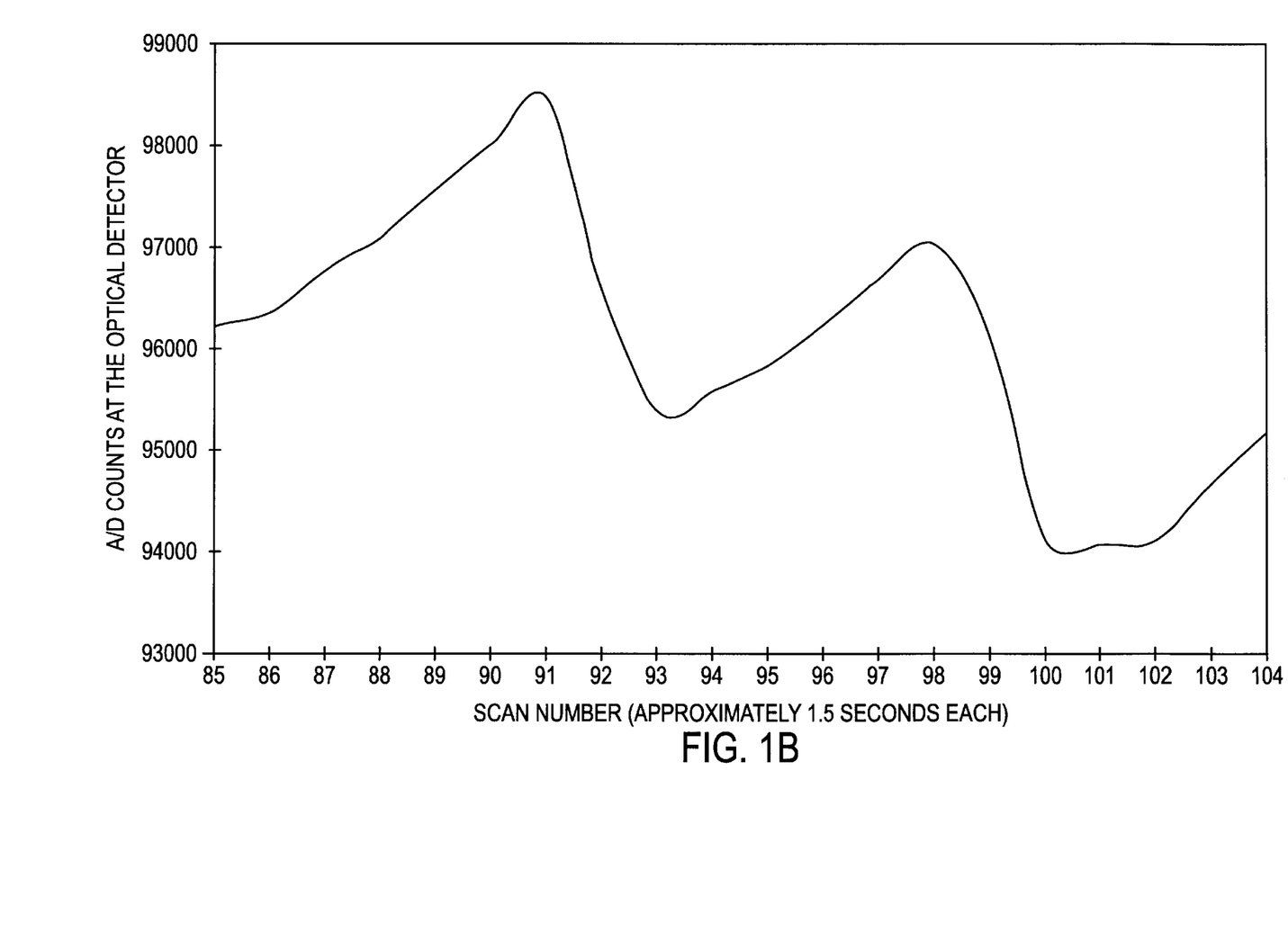

One phenomenon that has an affect on the accuracy of such a measurement is the minute expansion and contraction of the finger diameter in correlation with the beating of the heart, known as "pulse beat." This continuous and periodic pulse beat causes an artifact in optical measurement data, as shown in FIGS. 1A and 1B. These figures show a graph of A/D counts received for each "scan" of a subject's finger with a plurality of light wavelengths in sequence, as described generally in the '787 patent.

In such a measurement, light energy is directed into the finger at one side and detected quantitatively at the opposite side, first at a predetermined wavelength $y_1$, then at a predetermined wavelength $y_2$, and sequentially to predetermined wavelength $y_n$. The data for each of the n wavelengths is then used in an algorithm to obtain the quantitative analyte value. In order to reduce the effect of noise on the received data, multiple scans are taken and the data is averaged. Each scan requires many milliseconds. In an example instrument using 14 wavelengths, completion of one scan would require over 100 milliseconds. This period is a significant portion of the period of one pulse beat. A normal human pulse rate is typically between 70 and 100 beats per minute; one pulse beat is thus typically between 600 and approximately 860 milliseconds. Thus, the scan period typically would be between ⅙ and ⅛ of the pulse beat period.

Further, in addition to changing geometry, the finger's chemical constituency changes in a significant manner as blood is periodically forced through it by the heart during each pulse beat; consequently the quantitative light data received by the detector during any one scan have been subjected to varying light absorption conditions. This fact contradicts one of the key assumptions of Beer's Law (which states that the concentration of any organic chemical constituent is proportional to the optical absorption at all wavelengths) that the identical body chemistry is being measured at all wavelengths.

There thus exists a need in the art to eliminate the problems discussed above in achieving acceptable accuracy in noninvasive quantitative blood analyte measurement, which are caused by the spectral interference of pulse beat, and the varying body chemistry present during measurement by different wavelengths within any one scan.

SUMMARY OF THE INVENTION

The present invention solves the above-mentioned problems by providing a method for noninvasively determining the concentration of a blood analyte in a subject by transmitting light energy of at least one predetermined wavelength into a body part and measuring light energy emitted from the body part, including the step of correcting the measurement of light energy by modifying measurement data to take into account changes in body geometry and/or body chemistry as a function of time. The step of correcting preferably includes the steps of mathematically transforming data received representing light energy transmitted through the body part by fitting said data to a predetermined mathematical series, and eliminating from the series terms associated with changing body geometry and/or body chemistry.

According to another aspect, light energy of multiple wavelengths is sequentially transmitted through the body part over a predetermined period of time, and the step of correcting comprises the step of interpolating data received over the predetermined period of time to a preselected constant point in time.

In another embodiment of the invention, a device is provided for monitoring the blood glucose level of a patient, including an IRED for emitting light energy at a predetermined wavelength into the body of the patient at a particular location, a detector for detecting light energy transmitted through that location and producing signals corresponding thereto, a controller for determining the pulse rate of the patient from the signals, and for determining the existence of a blood glucose level approaching a hypoglycemic state based on the signals and the pulse rate, and for producing an output indicative of said blood glucose level, and an alarm that receives the output signal and outputs an alarm to warn the patient of the approaching hypoglycemic state.

DETAILED DESCRIPTION OF THE PREFERRED EMBODIMENTS

According to the invention utilizing near-IR transmission analysis techniques, near-IR light energy at bandwidths centering on one or more wavelengths of interest is transmitted through a blood-containing portion of the body of a test subject. In a preferred embodiment, the near-IR bandwidth is from 600–1100 nm, and preferably 700–1037 nm. The near-IR energy emerges from the test subject, generally opposite from the near-IR source, and is measured by a detector. Following amplification of the detector-generated signal, the output is processed into an output signal indicating the concentration of a particular analyte in the subject's blood, such as the level of glucose in the blood in mg/dL.

The plurality of IREDs (infrared emitting diodes) can be sequentially pulsed on and off so that the detector receives radiant energy transmitted from only one IRED at a time. Alternatively, a group of IREDs with narrow bandpass filters having identical wavelength output can be pulsed. It has been found that very accurate quantitative analysis blood glucose levels can be made with NIR energy at wavelengths within the range of 600 to 1100 nanometers.

Figure 2:
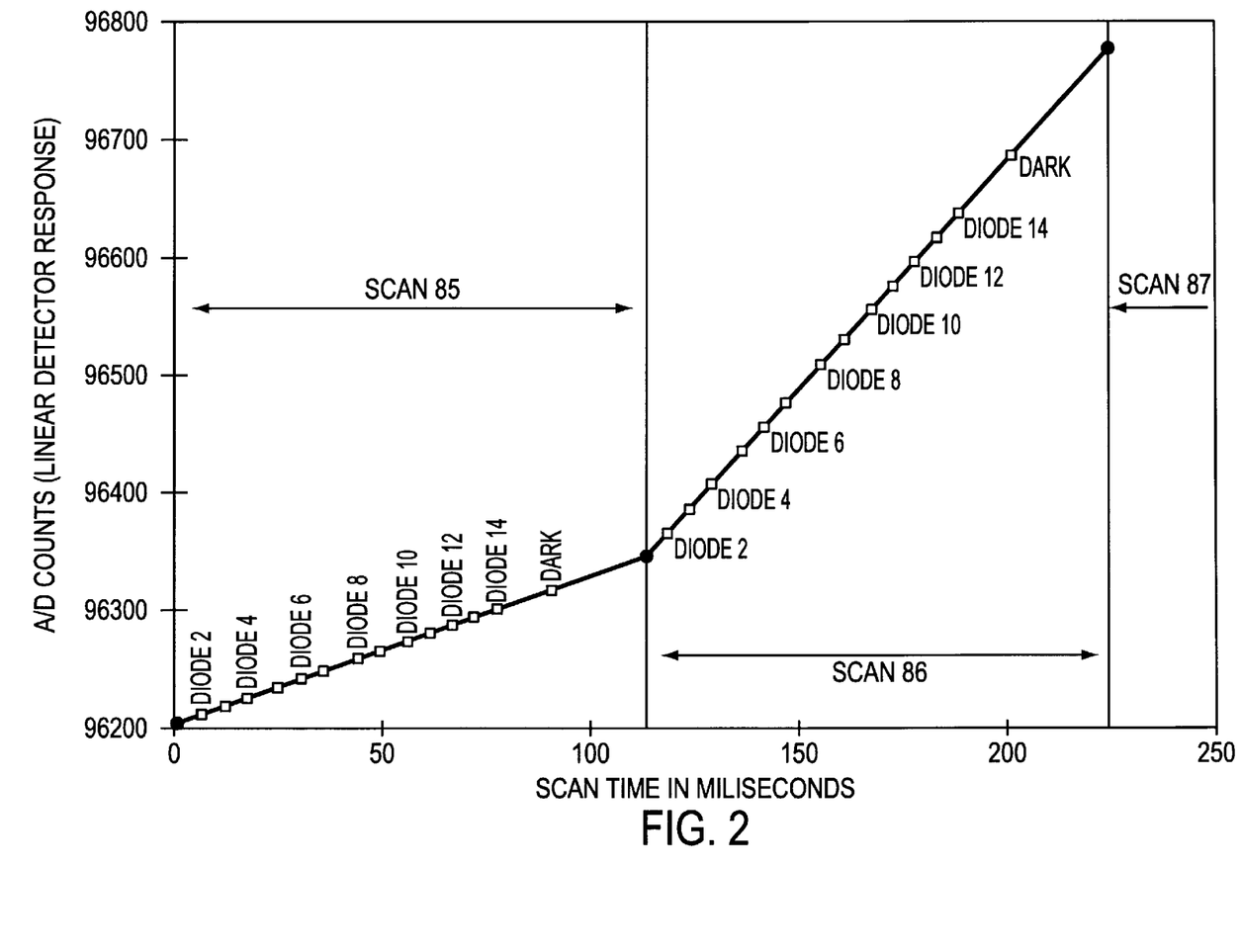
FIG. 2 is a graph illustrating the time difference associated with different scans.

FIG. 2 illustrates the differences in acquired quantitative optical data between two consecutive scans, wherein each scan consists of sequential irradiation by a plurality of IREDs each at a different wavelength. FIG. 2 represents the same data as shown in FIGS. 1A and 1B for scans 85 and 86. As shown in FIG. 2, the noninvasive measurement instrument incorporates 14 IREDS, each producing light energy at a different wavelength.

The scan begins by measuring the light transmitted through the finger at the first wavelength (by Diode 1) for a predetermined period of time, followed by measurements for the second through fourteenth wavelengths (produced by Diode 2 through Diode 14), and then a "dark" measurement period to provide a reference for removing background noise. The length of time that a particular diode is turned on can vary from that of other diodes, and is inversely related to the actual energy measured by the detector for each diode. The next scan then begins by repeating the same sequence. As shown in FIG. 2, the data measured by scan 86 is appreciably different from the data measured by scan 85. This difference is caused by the pulse beat and changing body chemistry in the finger as discussed above.

Figure 3:
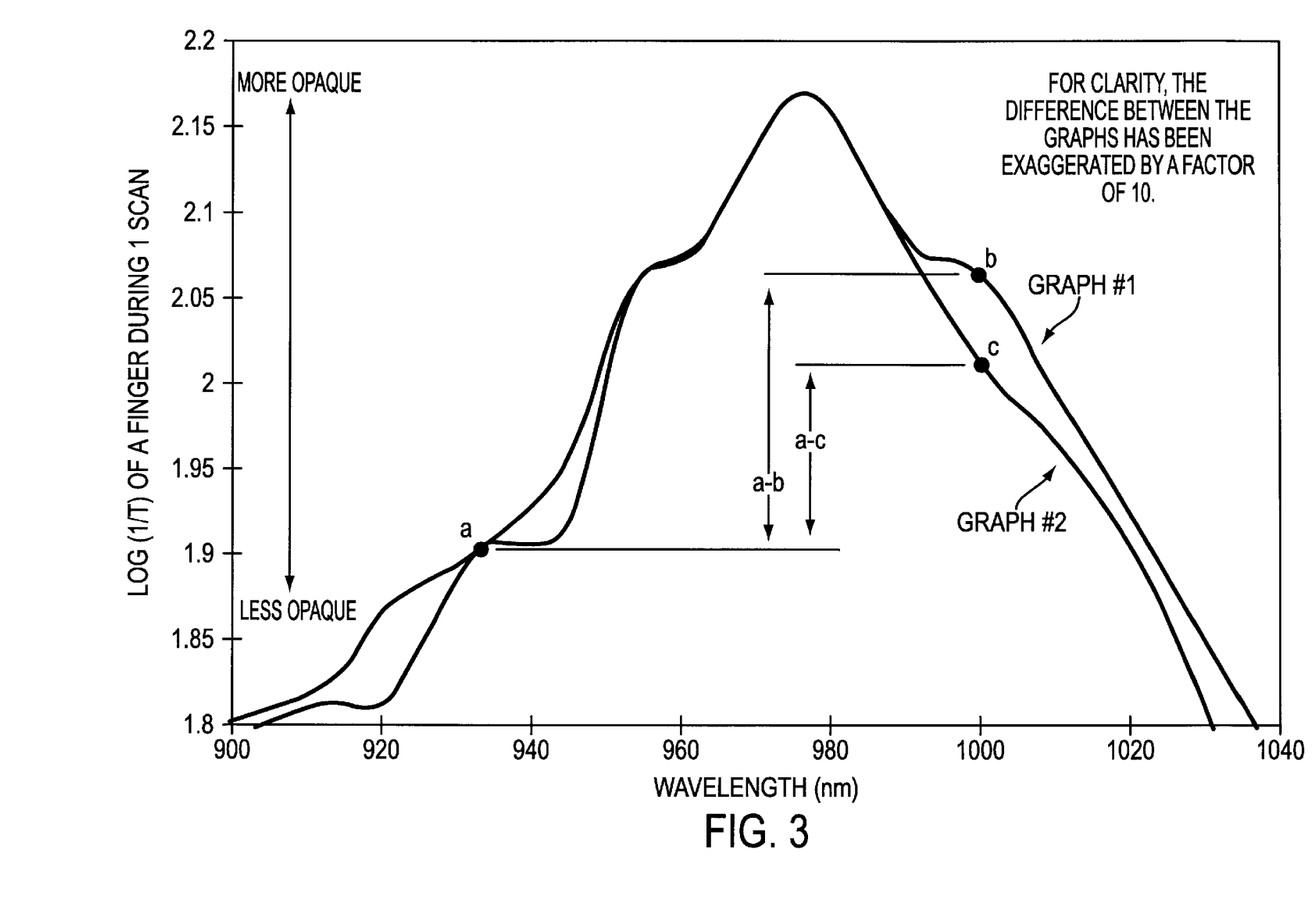
FIG. 3 is a plot of the spectrum of light energy transmitted through a subject's finger assuming simultaneous multiple wavelength measurements.

The problem in achieving acceptable accuracy is illustrated in FIG. 3. FIG. 3 shows the spectrum of light transmittance through a finger, in log (1/T), where T is equal to the fraction of light transmitted at a particular wavelength. Graph #1 represents the spectrum of transmitted light (inverted such that higher values represent less light transmitted through the finger, and lower values represent more light transmitted through the finger), assuming that all wavelengths are transmitted at the same instant in time. A conventional method for calculating a quantitative value involves subtracting the optical data at wavelength "a" from the data at wavelength "b."

Graph #2 in FIG. 3 shows the spectrum of measured optical data when the multiple wavelengths were measured sequentially during the time period shown in FIG. 2. The difference between the spectra is caused by changes in finger geometry during the pulse beat interval corresponding to the scan period. Here, the difference (on a logarithmic scale) between the correct value a–b and the actual value a–c for sequentially obtained data, is significant.

Figure 10:
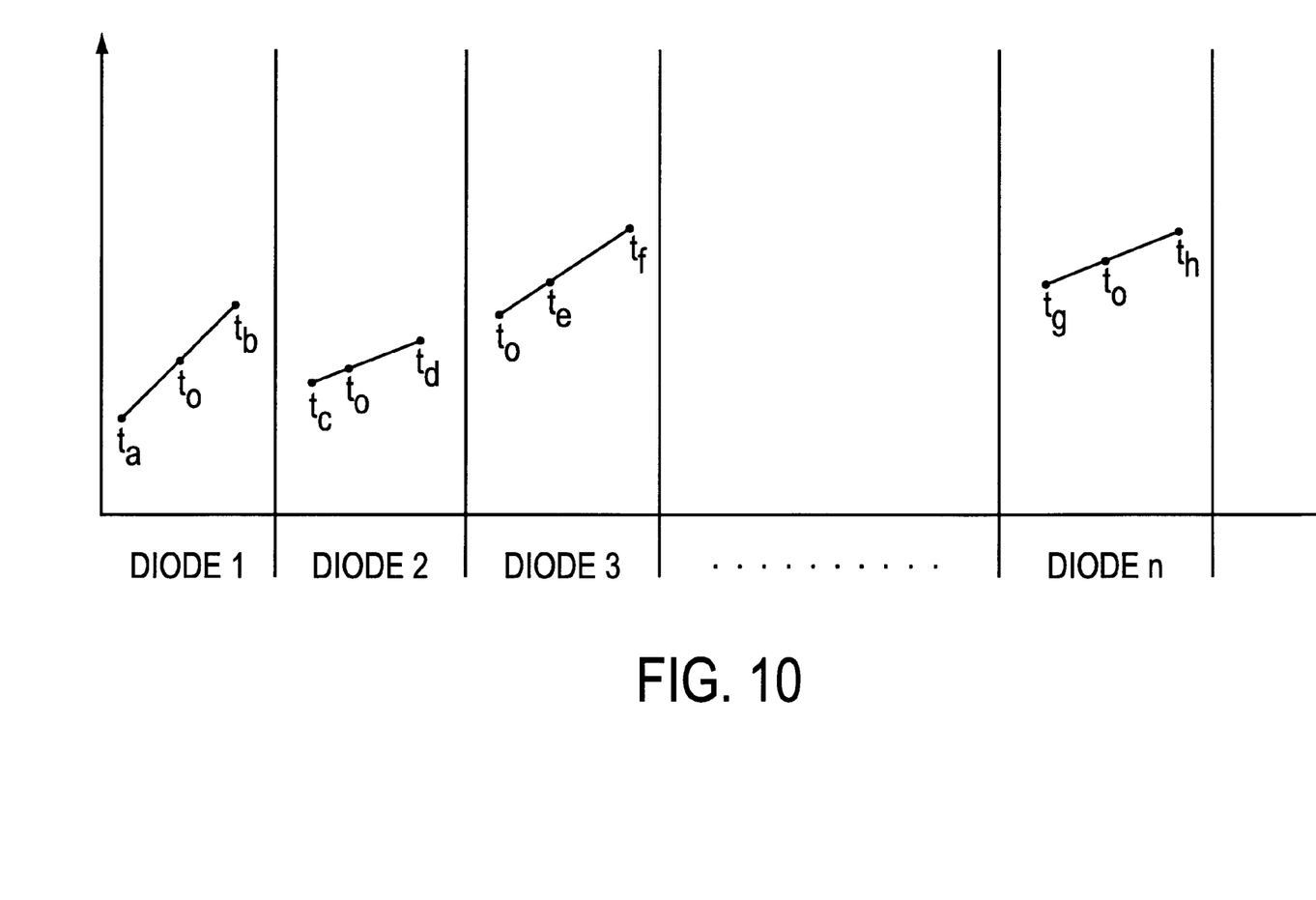
FIG. 10 is a chart illustrating a time difference interpolation process according to the present invention.

The error caused by the difference in time between the measurements can be compensated for by linearly interpolating the different values at each wavelength as a function of time. Given the light transmission values at each wavelength (produced by each diode) and the time at which those values were recorded, one can construct a hypothetical measurement of each wavelength as if all wavelengths were measured simultaneously. FIG. 10 illustrates an example of linear interpolation of two sequential scans performed by n diodes. Recording the optical values received at each time $t_1$–$t_n$ for diodes 1 through n, it is possible to linearly interpolate the values to the same point in time $t_0$, to thus obtain an interpolated spectrum representative of optical data received if all wavelengths were transmitted through the finger at the same instant. It is noted that for some measurements, such as illustrated for Diode 3, the time $t_0$ may be prior to the two actual measurements at times $t_e$ and $t_f$.

A second method according to the present invention for correcting quantitative measurement data for error caused by pulse beat is to carry out a sufficiently large number of contiguous scans and to determine an average of the resulting quantitative values. For example, 250 or more scans may be performed and the resulting data averaged to obtain quantitative measurement with increased accuracy. This approach assumes that the scan rate of the measurement instrument (e.g., scans per second) is fast enough to complete the measurement in a reasonable amount of time, e.g., 30 seconds. This approach further assumes that the data storage and data processing capacity of the instrument is sufficient to handle such an amount of data.

Figure 4A:
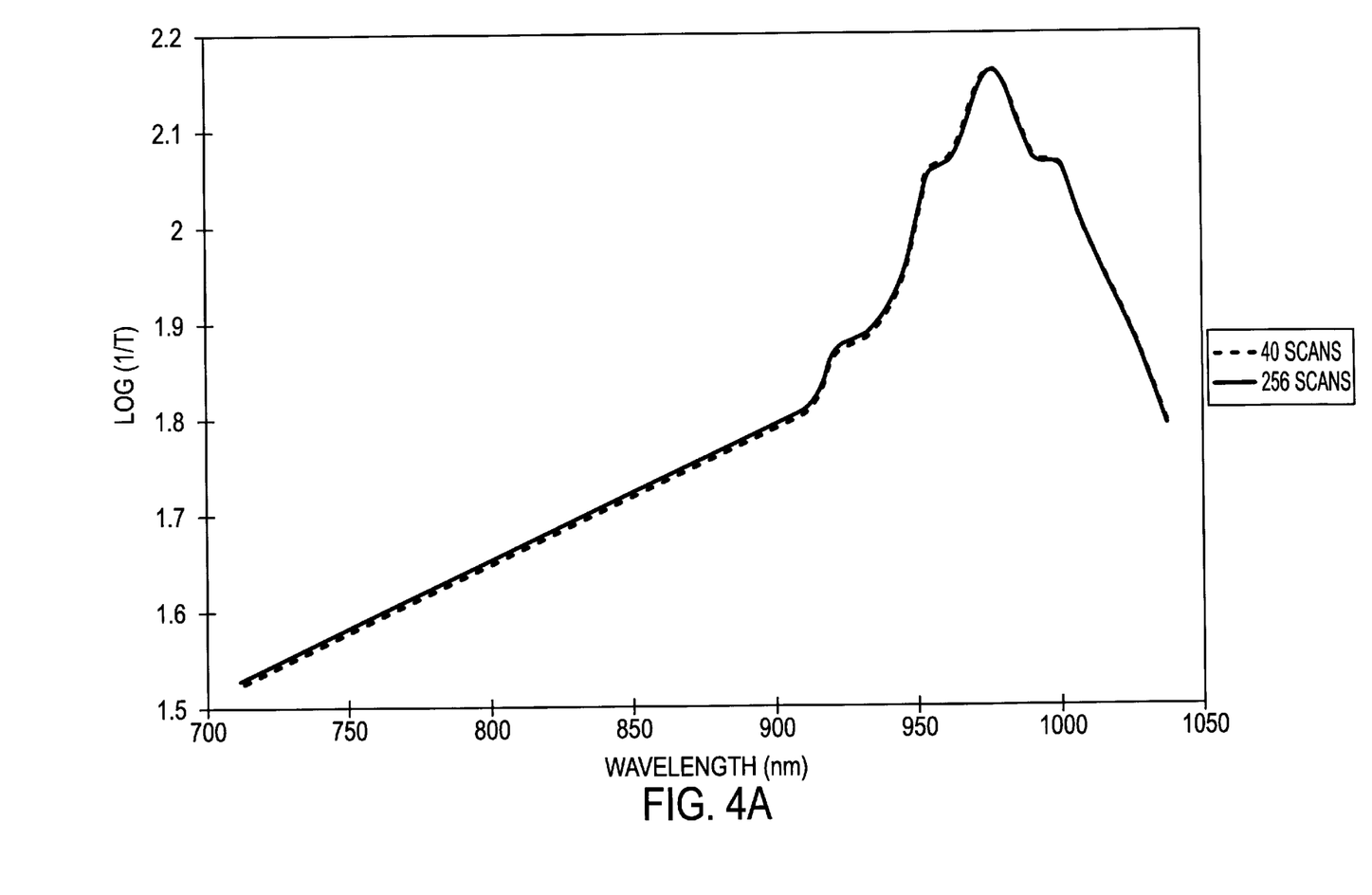
FIGS. 4A and 4B are plots of averages of multiple scans.
Figure 4B:
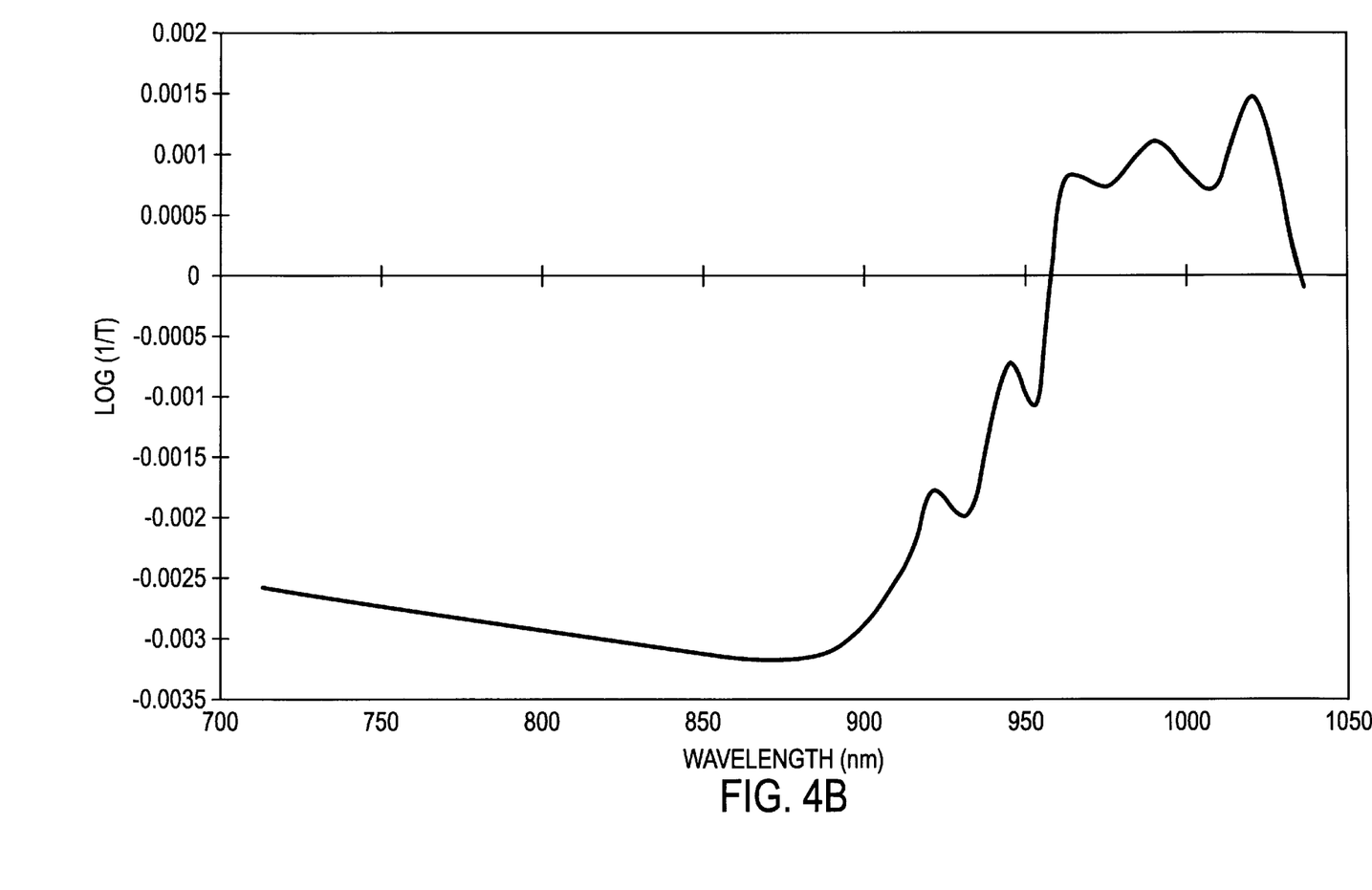

Increasing the number of scans to be averaged has a greater effect than simply averaging multiple measurements per se. A greater number of scans reduces the sampling error bias caused by starting and stopping measurement at an unknown phase of the heart beat cycle. FIG. 4A shows plots of 40 versus 256 scans, and FIG. 4B shows the difference between averaging 40 scans and averaging 256 scans. While on an absolute scale the difference might appear small, because the pulse beat phenomenon is regular, the differences are not random and have a significant deleterious effect on blood analyte (in particular blood glucose) concentration measurement.

Averaging a large number of scans in order to obtain a quantitative measurement thus truly averages out the disturbance caused by the pulse beat phenomenon. In a preferred embodiment using 14 different wavelengths, with a scan rate of six full scans per second, this number is approximately 256 scans.

In particular, if the pulse beat is assumed to be uniform, the collected spectral data are actually sub-samples or stratification samples of the pulse beat. For example, if the pulse beat were divided into seven segments, the data collected over seven scans would represent one complete scan in each segment. Because each segment would be represented, the sample would be unbiased. Likewise, data collected by N scans over any whole number N of pulse beats would represent N sub-samples in each 1/N segment of the pulse beat and the average would be unbiased. Unfortunately, it is not feasible to phase lock a scan to a pulse beat, in other words, to start the scan at the precise beginning of a pulse beat and end the scan at the precise end of the pulse beat. In practice, there will exist some over-represented strata in the optical data.

For example, if the scan starts in the sixth segment of a pulse beat divided into seven segments, and ends in the first segment of a later pulse beat, segments or strata 6, 7, and 1 will be over-sampled and the resulting average will be biased. The amount of bias thus is proportional to the reciprocal of the number of pulse beats sampled, or the reciprocal of the number of optical scans, as represented by the following expressions:

Bias $\propto$ (number of complete pulse beats sampled)$^{-1}$

Bias $\propto$ (number of optical scans)$^{-1}$

These two equations give the same result because as the number of scans increases, more complete pulse beats are measured.

Taking the average of multiples of a noisy signal normally improves the error by a factor of $(n)^{1/2}$ where n is the number of signal measurements taken. However, the pulse sampling error improves as a function of (n), which is the square of normal averaging improvement. Consequently, having a sufficient number of consecutive scans of the entire pulse beat provides a greater benefit than simply averaging a shorter multiple scan measurement. For example, at a typical pulse rate, 40 scans will cover approximately 6 to 7 complete pulse beats. Bias error is thus $\frac{1}{7}$ to $\frac{1}{6}$ of the pulse variability. When 250 scans are made, approximately 35–42 complete pulse beats. The sampling bias for 250 scans is thus $\frac{1}{42}$ to $\frac{1}{35}$ of the pulse variability. By thus increasing the number of scans to 250 or more, the sampling error becomes smaller than the desired accuracy in a blood glucose concentration measurement.

Figure 5:
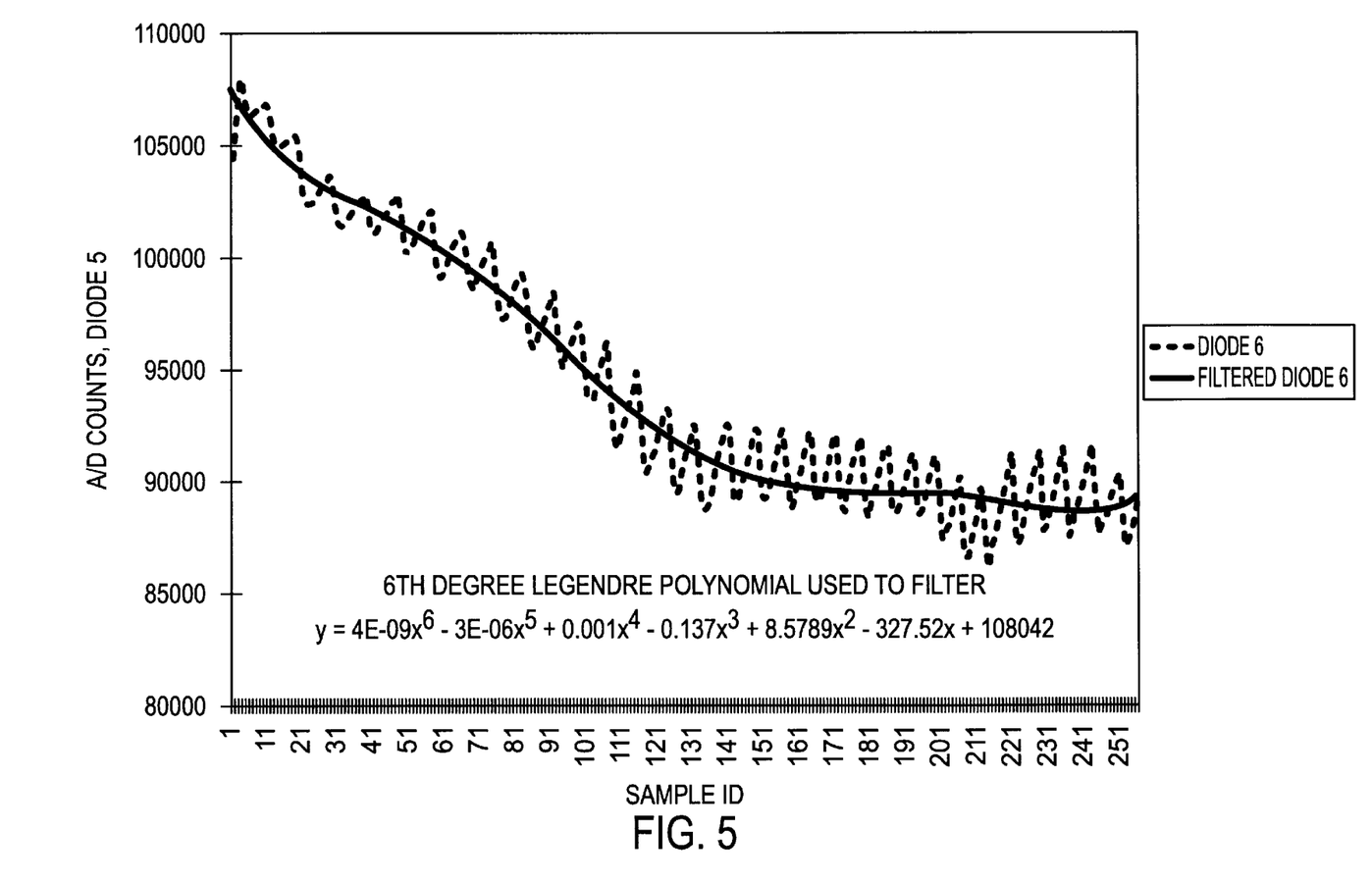
FIG. 5 is a graph of the effect of filtering on received optical measurement data, according to a preferred embodiment of the present invention.
Figure 6:
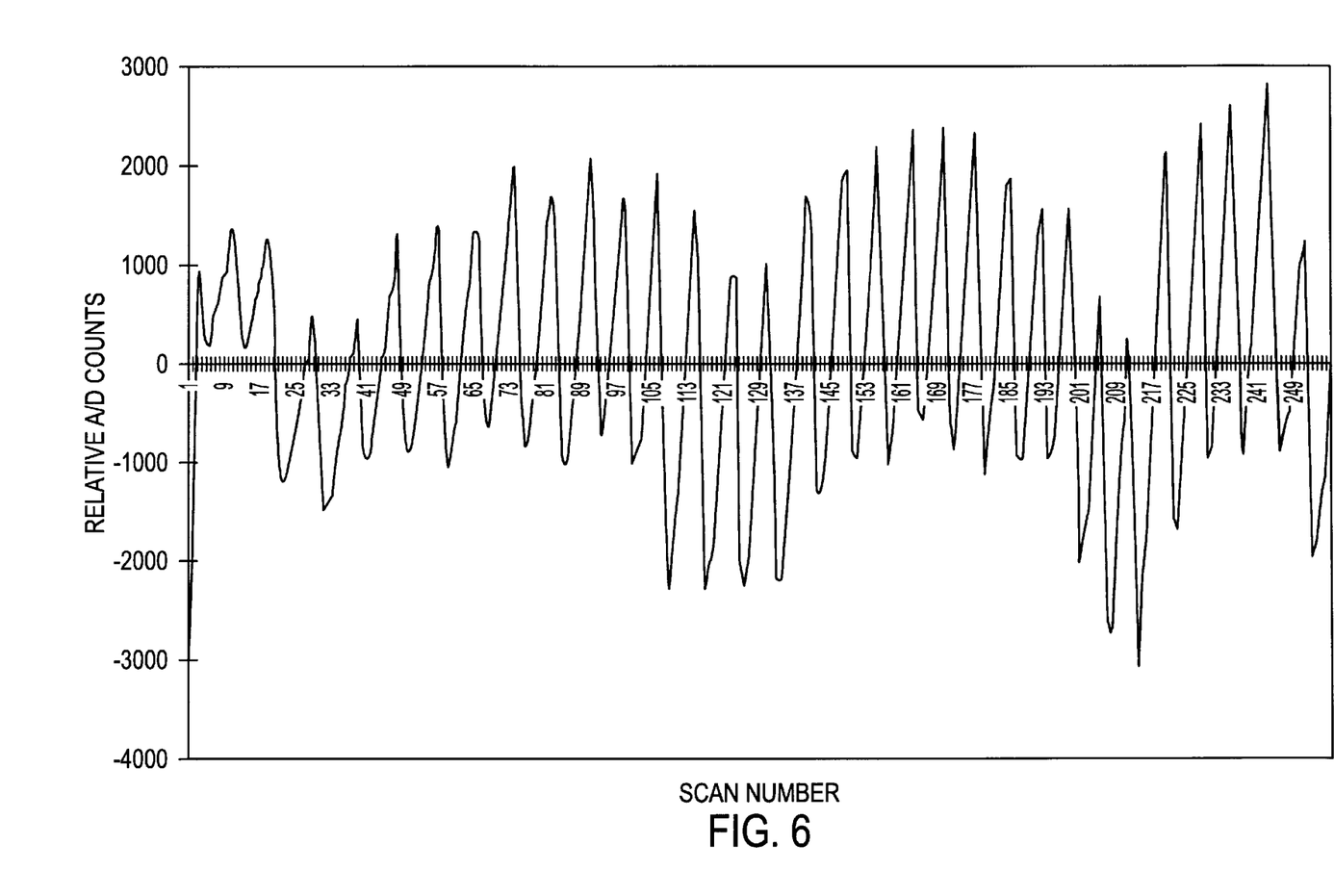
FIG. 6 is a graph showing the high frequency content of information received for a single wavelength at different scans.

FIGS. 5 and 6 illustrate an alternate method for removing from measurement data the interfering variations caused by the pulse beat phenomenon. According to this method, the measurement data are transformed by being fitted to a mathematical series such a Fourier series, Legendre series or similar series. By dropping or separating out from the resulting series certain terms, such as either low or high frequency terms, it is possible to filter out the faster (i.e., higher frequency) pulse beat modulations from the slow or steady state blood glucose or other analyte data.

As shown in FIG. 5, the unfiltered measurement data shown in dashed lines contains a high frequency noise component introduced by the pulse beat phenomenon. The raw data is transformed by fitting it to a sixth degree Legendre polynomial, and the higher frequency terms associated with pulse beat are eliminated from the series, resulting in the "clean" measurement data represented by the solid line. FIG. 6 illustrates the high frequency measurement data from a single wavelength (diode), which is dominated by the pulse beat effect. Thus, according to this embodiment, sufficient measurement data is obtained (such as by scanning for a sufficiently long time, e.g. 30 seconds) and transformed by a suitable mathematical series, and the high order terms of the resulting series are dropped to obtain accurate measurement data without interference from pulse beat.

Figure 7:
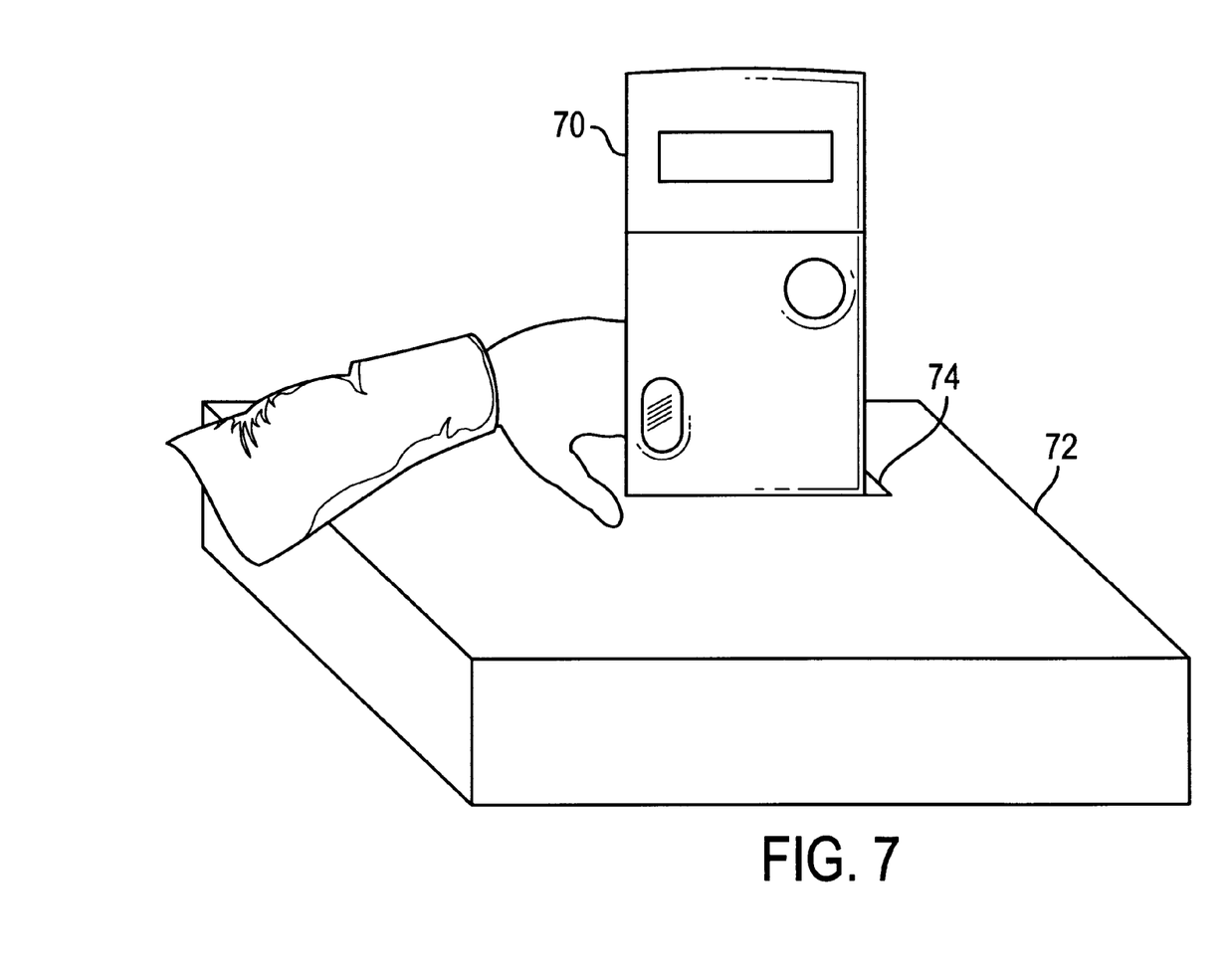
FIG. 7 is a diagram of a stand used in conjunction with a noninvasive blood analyte measurement instrument to eliminate inaccuracies caused by motion of the subject according to one aspect of the present invention.

In accordance with the present invention, it is important to preclude errors being caused by finger or body motion during a measurement procedure, in addition to elimination of pulse beat error. This is especially true for measurement procedures which require a relatively long period of time, such as 30 seconds, during which a subject may find it increasingly difficult to remain essentially stationary. Any motion of the body or finger that disturbs the measurement field causes unacceptable degradation in the accuracy of the measurement. While handheld instruments such as disclosed in the above-referenced U.S. patents are acceptable when measurements on the order of 10 seconds are used, for the longer measurement periods contemplated by the present invention, use of a handheld instrument is very likely to introduce unwanted artifacts caused by motion of the finger or body of the subject during the measurement period. To reduce the possibility of such errors, a stand 72 is provided as shown in FIG. 7, which has a slot 74 for receiving a noninvasive measurement instrument 70. Stand 72 may be made of low-cost foam rubber or equivalent material, and may be placed on a table, counter, desk, or other suitable flat horizontal surface. The subject's hand can be rested on the stand while the subject's finger is inserted in the instrument for measurement to be performed. Alternatively, the instrument 70 may be designed to be self-standing on a flat surface, such as by modifying the base so that it is flat. Additionally a weighted base may be used to alter the center of gravity of the instrument such that it will not tip over when placed upright on a flat horizontal surface.

In each of the methods disclosed above for eliminating noise caused by the pulse beat phenomenon, it has been assumed that Beer's law (i.e., log 1/T) mathematics is used to measure the absorption spectrum and calculate glucose (or other blood analyte) concentration. Using Beer's law, a near-infrared calibration is developed by regressing a series of absorbance measurements made at multiple wavelengths against an analyte such as blood glucose. The regression results are made more statistically significant by dropping statistically insignificant terms (i.e., wavelengths) from the regression equation. However, in reducing the number of wavelengths in the regression, some part of the measurement signal is lost; additionally, the averaging effect of making multiple (albeit statistically redundant) measurements in reducing noise is lost to the extent that wavelength terms are dropped.

An alternative mathematical approach to concentration calculation is the Hadamard transformation. The Hadamard transformation enables the number of terms in the regression equation to be reduced, without loss of the signal content and benefit of measurement averaging under the Beer's law approach. The Hadamard transformation requires that analyte absorbance at a combination of wavelengths be used in the calculation of concentration, as opposed to the absorbance at a single wavelength under Beer's law.

The simplest Hadamard matrix takes the form:

1,1
−1,1

For powers of 2, the Hadamard matrix can be represented as:

H,H
−H,H where H is any Hadamard matrix. Thus, to transform a two wavelength measurement, the two term measurement vector is multiplied by the 2×2 Hadamard matrix, and the resulting two term Hadamard-transformed variable is used in place of the original wavelength variable.

For example, the Hadamard transform of the absorbance data measured at two wavelengths $A_1$ and $A_2$ would be equal to:

$$H_1 = A_1 - A_2$$

$$H_2 = A_1 + A_2$$

where $H_1$ and $H_2$ are the two Hadamard-transformed variables.

In the above example, a regression performed using the two individual absorbance measurements at each wavelength under the Beer's law and Hadamard approaches would achieve the same results. However, if one of the terms is found to be not statistically significant and thus should be dropped, under Beer's law the averaging effect would be lost, while under the Hadamard approach the beneficial effect of averaging would be maintained. This is because each Hadamard term is the combination of two measurements and thus measurement noise is averaged. Further, each Hadamard term contains some of the information present at the other wavelength. Hadamard-transformed variables are more robust in the regression because there is much less covariance between them than in the original absorbance data (which inevitably is highly covariant). Finally, because the most common way to measure absorbance spectrally is to measure the absorbance at two points in the spectrum and take the difference (see FIG. 3), the Hadamard approach represents a more compact way to express difference signals (e.g., term $H_1$) with fewer terms.

The two wavelength example above can of course be extended to multiple wavelength measurements, where the averaging improvement in noise, reduction in the number of terms in the regression, and preservation of measurement information become more important as more wavelengths are measured.

Calibration

In the preferred embodiment of the invention, an optical instrument is used to transmit light energy at multiple (i.e., 14) wavelengths through the most distal portion of the index finger, and to measure quantitatively the light energy transmitted at the opposite side of the finger. Each instrument is individually calibrated to the makeup of the individual for which the instrument will be used, in order to achieve the most accurate measurements.

Approximately 99% of the human body's tissue is composed of water, fat and protein, with the relative proportions of these three constituents varying throughout the body. At any particular location in the body these proportions also vary as a function of time. As an example, compositional changes associated with water loss from respiration (such as during exhalation) in a typical adult is approximately 0.7 quarts (or 1.5 lbs.) per day. Even more significant is water loss from perspiration, even aside from strenuous exercise. For example, driving a car without air conditioning during a warm summer day can result in water loss of one quart (or 2 lbs.) per hour. Over longer periods of time, the effects of diet and exercise can change significantly both the relative and absolute amounts of water, fat and protein (muscle) in the body.

The concentrations of various blood analytes are minuscule as compared with the concentrations of water, fat and protein in the body. Near-IR absorption due to water is by far the most significant of any constituent absorption. Consequently, successful NIR calibration of a noninvasive quantitative measurement instrument for blood analytes must fully take into account the effects of water, fat and protein on the absorbance spectrum. In order to obtain accurate, meaningful measurements into the future, the instrument must achieve a robust calibration that covers all reasonable chemical and optical variances that the instrument is expected to encounter over time. For blood analytes, this means that different proportions and quantities of water, fat and protein must be included in such a calibration.

It has been discovered by the present inventors that calibration of an optical measurement instrument can be made more rapidly and more robustly by measuring multiple fingers of the individual for which the instrument will be used, during the calibration process. Each finger of an individual differs in the level of water, fat and protein it contains, and each finger changes the concentrations of these constituents at different rates. Measurement of different fingers thus multiplies the effective time and number of samples for calibration. For just one laboratory measurement of glucose level, the optical measurement of two, six or all ten fingers speeds the calibration, increases sample diversity, and reduces the number, and thus the discomfort and cost associated with reference measurements taken invasively.

In the preferred embodiment, measurement of six fingers (index, middle and ring) of a subject are made during calibration, which thus provides calibration information for six different samples, with each finger providing different concentrations of water, fat and protein, as well as unique geometry and optical path length, thus providing robustness and enhancing future prediction capability. In contrast, obtaining equivalent results through measurement of only one finger would require multiple invasive measurements over a much longer period of time.

Hypoglycemia Monitor and Alarm

For persons with severe cases of diabetes, there exists a risk of life-threatening low blood glucose levels (i.e., hypoglycemic levels) while they sleep. For some of these individuals, they must be awakened several times during the night to have their blood glucose level tested.

Figure 8:
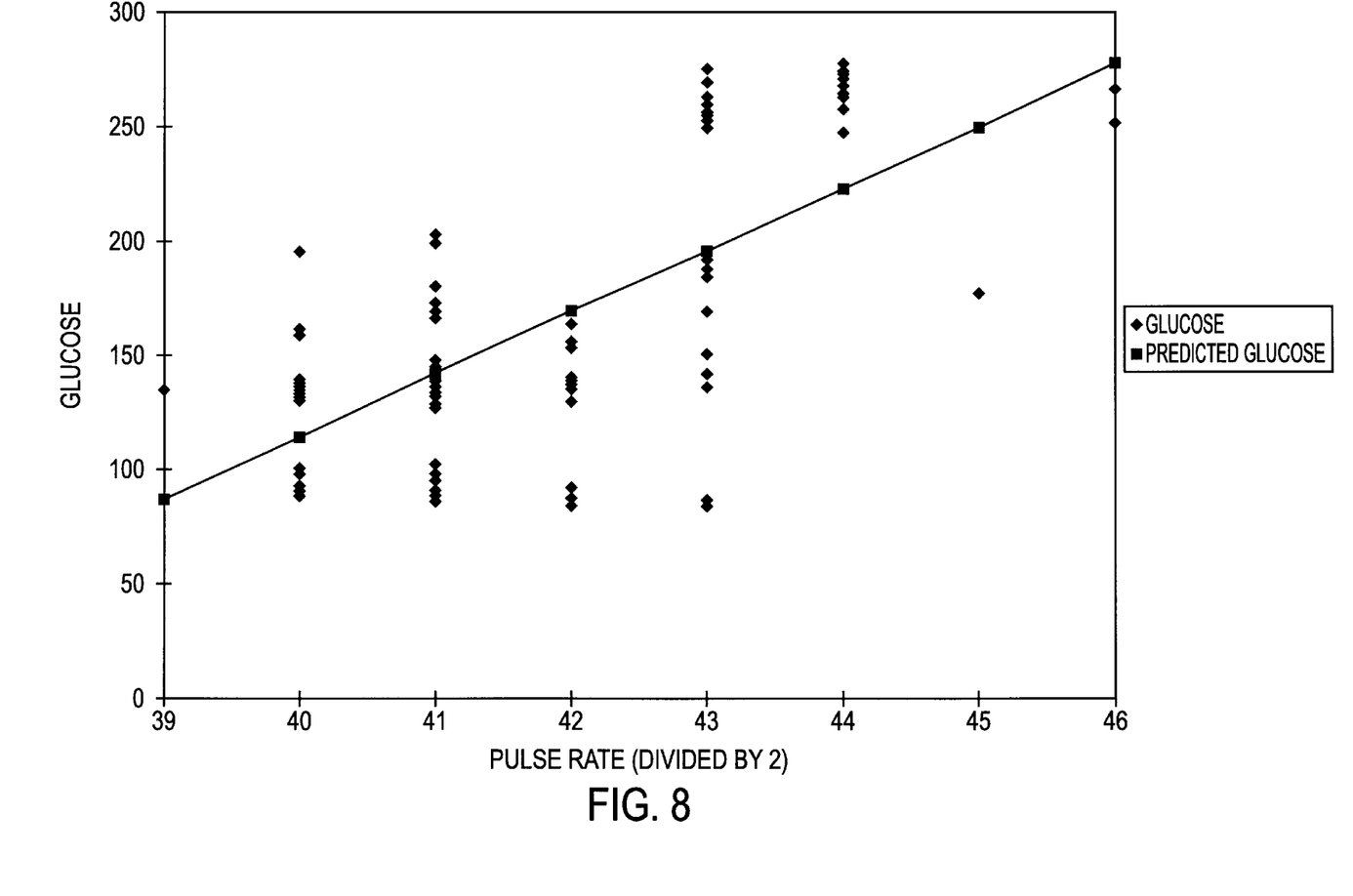
FIG. 8 is a first graph showing the correlation of pulse count to glucose level.
Figure 12:
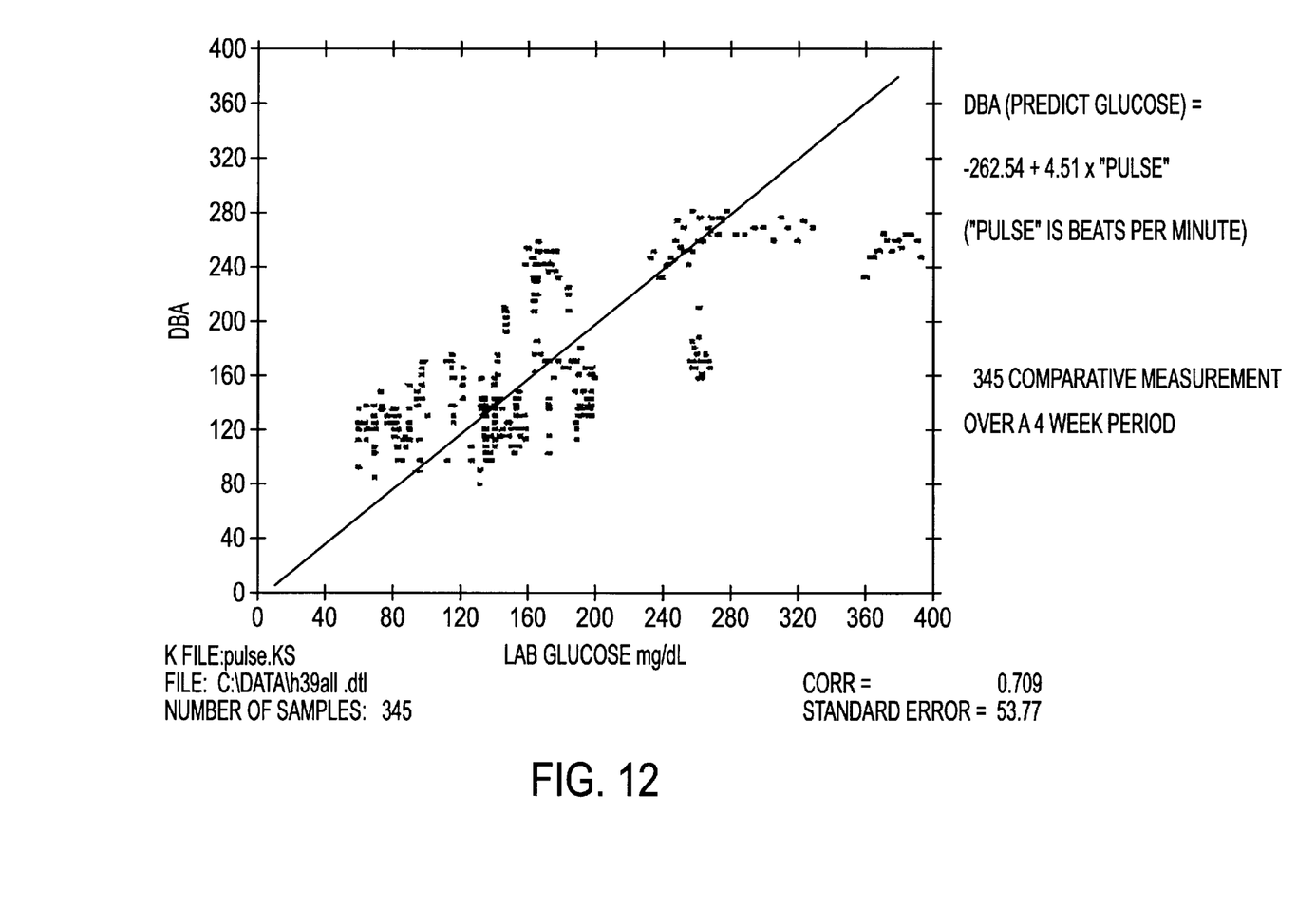
FIG. 12 is a second graph showing the correlation of pulse count to glucose level.

The present inventors have unexpectedly discovered, in conjunction with the methods discussed above, that for diabetics, there exists a correlation between pulse rate and blood glucose level as the blood glucose level drops. Specifically, it has been found by the present inventors that as blood glucose concentrations in persons with diabetes approach hypoglycemia levels, their pulse rate becomes significantly slower. As shown by FIG. 8, there is a significant correlation of blood glucose level to pulse rate in persons with low blood sugar. This correlation is over R=0.68 and has appeared to be consistently near that value from person to person with low blood sugar. Additionally, as shown in FIG. 12, the present inventors have found that pulse rate alone may be used as a statistical predictor of blood glucose levels over a larger range.

Figure 9A:
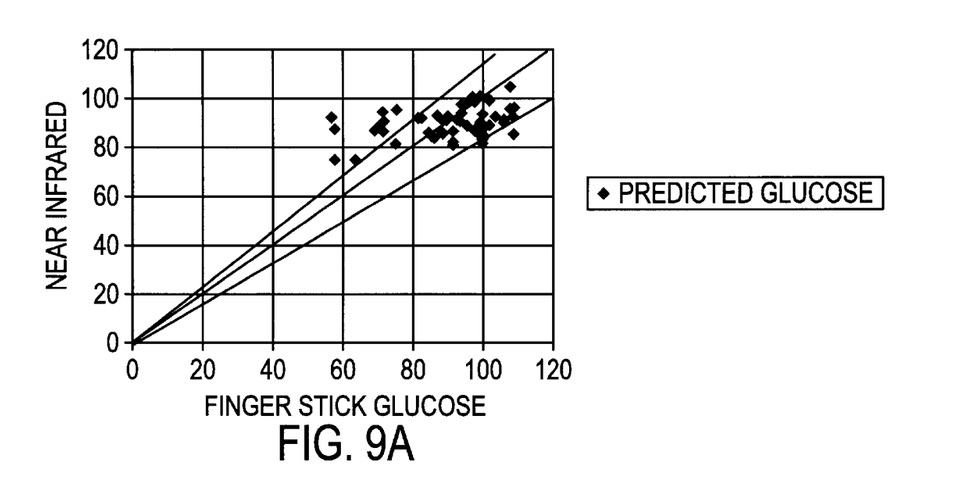
FIGS. 9A and 9B are plots of the correlation of pulse beat with glucose concentration in the blood.
Figure 9B:
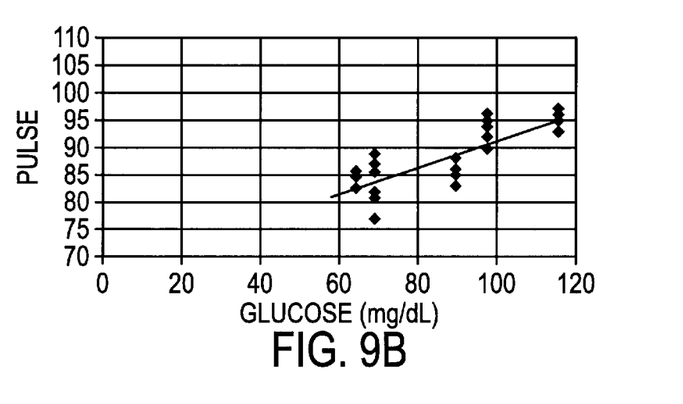

As disclosed above, signal filtering techniques such as Fourier or Legendre transforms can separate the pulse beat signal from the remainder of the measurement data in an optical absorbance measurement. A common symptom in persons with low blood sugar is hand tremor, which causes defects in the absorbance spectrum measured by the noninvasive optical instrument when such person attempts to use the instrument. To compensate for this situation, the present invention provides a technique for combining pulse beat information (as isolated from optical measurement data by mathematical transformation as disclosed above) with measured optical data to maintain high accuracy in glucose level measurement at low blood sugar levels. FIG. 9A shows a graph of the correlation at low blood sugar levels of predicted glucose concentration to actual glucose level measured invasively, where the predicted levels are obtained by noninvasive measurement without taking pulse beat into consideration. FIG. 9B shows a graph of the correlation at low blood sugar levels of predicted glucose level to actual glucose level when pulse rate is taken into account. As shown, use of the pulse rate information at low blood sugar levels diminishes the degradation in accuracy of the measurement at such levels.

Figure 11:
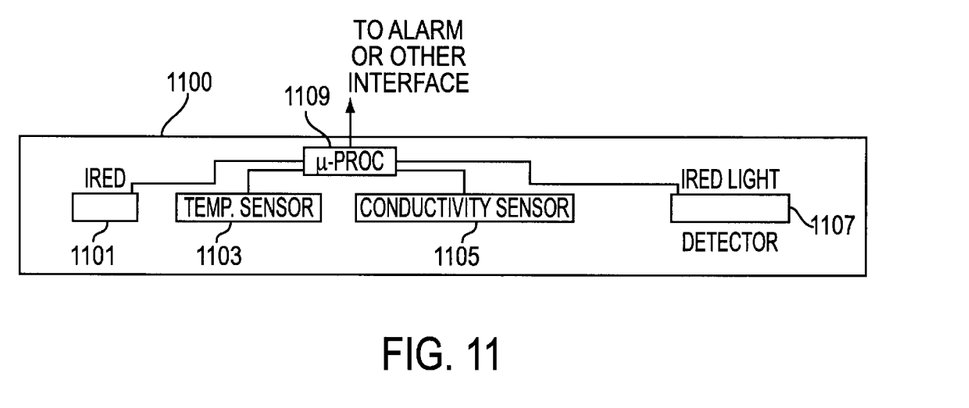
FIG. 11 is a diagram of a wristband monitor and alarm incorporating the methods of the present invention.

A further advantage made possible by the present invention is the use of a simple wristband type of monitor and alarm 1100, as shown in FIG. 11. A single IRED 1101 is used in a rapid pulsating mode to measure pulse beat, in conjunction with a microprocessor 1109 and IRED detector 1107. The wristband monitor is calibrated to emphasize the detection of low blood sugar levels. In a preferred embodiment, a temperature sensor 1103 and a skin conductivity sensor 1105 are provided to measure the temperature and conductivity of the skin. These parameters in addition to the pulse beat information are used to detect a dangerous low blood sugar level in the subject. Upon such detection, the microprocessor 1109 sends a signal to an alarm (not shown). According to a further embodiment, the microprocessor sends an alarm signal to an interface, which interface could control the operation of potentially dangerous machinery being operated by the subject. In this way, a person with diabetes who would be experiencing a low blood sugar episode while operating potentially dangerous machinery, such as driving an automobile or operating factory equipment, would be alerted to the impending danger of a hypoglycemic condition, and if the person were unable to respond, the machinery could be safely shut down in an appropriate manner, thus preventing potential harm or damage.

The invention having been thus described, it will be apparent to those skilled in the art that the same may be varied in many ways without departing from the spirit and scope of the invention. Any and all such modifications are intended to be included within the scope of the following claims.

What is claimed is:

1. In a method for noninvasively determining the concentration of a blood analyte in a subject by transmitting light energy of at least one predetermined wavelength into a body part and measuring light energy emitted from the body part, the improvement comprising:

correcting the measurement of light energy by modifying measurement data to take into account changes in body geometry and/or body chemistry as a function of time, by mathematically transforming data received representing light energy transmitted through the body part by fitting said data to a predetermined mathematical series, and eliminating from said series terms associated with changing body geometry and/or body chemistry.

2. The method of claim 1, wherein said mathematical series is a Fourier series.

3. The method of claim 1, wherein said mathematical series is a Legendre series.

4. The method of claim 1, wherein light energy of multiple wavelengths is sequentially transmitted through said body part over a predetermined period of time, and the step of correcting comprises the step of taking a predetermined number of repeated measurements of said multiple wavelengths over an extended predetermined period of time, wherein said predetermined number is selected such that a sampling error caused by said time varying changes in body geometry and/or chemistry becomes smaller than a desired accuracy level of said measurement.

5. The method of claim 1, wherein said method is performed by using a noninvasive quantitative optical measurement instrument, and said method further includes inserting said instrument into a stand prior to performing said measurement.

6. The method of claim 1, further comprising the step of transforming measurement data by using a Hadamard matrix transformation.

7. The method of claim 1, wherein said correcting step corrects for changes to said body part caused by pulse beat.

8. The method of claim 7, wherein said correcting step includes the step of correlating pulse beat data with blood analyte measurement data.

9. The method of claim 8, wherein said blood analyte data represents glucose concentration.

10. The method of claim 9, wherein said method is performed by an instrument including an IRED and an IRED detector, placed around the wrist of a subject.

11. The method of claim 9, wherein said method is performed by an instrument including an IRED and an IRED detector, placed around the finger of a subject.

12. The method of claim 1, further including the step of calibrating said measurements by performing an invasive measurement of blood analyte in conjunction with noninvasive optical measurement of a plurality of fingers of a subject.

13. In a method for noninvasively determining the concentration of a blood analyte in a subject by sequentially transmitting light energy of multiple wavelengths into a body part over a predetermined period of time, and measuring light energy emitted from the body part, the improvement comprising:

correcting the measurement of light energy by modifying measurement data to take into account changes in body geometry and/or body chemistry as a function of time wherein light energy of multiple wavelengths is sequentially transmitted through said body part over a predetermined period of time, and the step of correcting comprises the step of interpolating data received over said predetermined period of time to a preselected constant point in time.

14. The method of claim 13, wherein said step of interpolating comprises linear interpolation.

* * * * *